United States Patent
Pancholi

(10) Patent No.: US 10,973,975 B1
(45) Date of Patent: Apr. 13, 2021

(54) METHOD OF EXTRACTING FROM THE PATIENT'S OWN BLOOD ENRICHED PLATELET FACTORS (ENPLAF) AND APPLICATION THEREOF IN TREATMENT OF VARIOUS MEDICAL CONDITIONS

(71) Applicant: Nishit Pancholi, Fremont, CA (US)

(72) Inventor: Nishit Pancholi, Fremont, CA (US)

( * ) Notice: Subject to any disclaimer, the term of this patent is extended or adjusted under 35 U.S.C. 154(b) by 312 days.

(21) Appl. No.: 15/863,861

(22) Filed: Jan. 5, 2018

Related U.S. Application Data

(60) Provisional application No. 62/442,660, filed on Jan. 5, 2017.

(51) Int. Cl.
| | |
|---|---|
| *A61M 1/36* | (2006.01) |
| *A61P 21/00* | (2006.01) |
| *A61P 19/08* | (2006.01) |
| *A61K 35/19* | (2015.01) |

(52) U.S. Cl.
CPC ........... *A61M 1/3693* (2013.01); *A61K 35/19* (2013.01); *A61M 1/3687* (2013.01); *A61P 19/08* (2018.01); *A61P 21/00* (2018.01); *A61M 2202/0427* (2013.01)

(58) Field of Classification Search
CPC .............. A61M 1/3693; A61M 1/3687; A61M 2202/0427; A61M 1/3689; A61M 1/369; A61M 1/385; A61P 21/00; A61P 19/08; A61K 35/19
See application file for complete search history.

(56) References Cited

U.S. PATENT DOCUMENTS

| | | | |
|---|---|---|---|
| 5,428,008 A * | 6/1995 | Chao ................... | A61K 9/1271 514/13.9 |
| 2012/0230968 A1* | 9/2012 | Worden, Sr. ........... | A61K 35/19 424/93.72 |
| 2015/0004079 A1* | 1/2015 | Hassouneh .......... | G01N 1/4077 422/533 |
| 2016/0235889 A1* | 8/2016 | Pallotta ............... | A61L 27/3604 |

OTHER PUBLICATIONS

Dhurat R, Sukesh M. Principles and Methods of Preparation of Platelet-Rich Plasma: A Review and Author's Perspective. J Cutan Aesthet Surg. 2014;7:189-197 (Year: 2014).*

* cited by examiner

*Primary Examiner* — Nicholas J Weiss
*Assistant Examiner* — Alessandro R Del Priore
(74) *Attorney, Agent, or Firm* — Steven Ivy P.C.

(57) ABSTRACT

Disclosed is a method of extracting, from the patient's own blood, enriched platelet factors, or EnPLAF, storable supernatant, void of live blood cells, utilized for treatment of said patient's medical conditions, including but not limited to pain management, aesthetic rejuvenation, bone, muscle and soft tissue healing.

1 Claim, 7 Drawing Sheets

METHOD OF EXTRACTING FROM THE PATIENT'S OWN BLOOD ENRICHED PLATELET FACTORS (ENPLAF) AND APPLICATION THEREOF IN TREATMENT OF VARIOUS MEDICAL CONDITIONS

RELATED PATENT APPLICATION

The present Non-Provisional U.S. Patent Application claims the priority from U.S. Provisional Patent Application No. 62/442,660 filed on Jan. 5, 2017, the subject matter of which is incorporated herein by reference.

FIELD OF INVENTION

The present invention relates to the general field of medical devices designed for extraction of human platelet growth factors and methods of using said platelet growth factors for treatment of various medical conditions.

BACKGROUND OF THE INVENTION

Unless otherwise indicated herein, the materials described in this section are not prior art to the claims in this application and are not admitted to be prior art by inclusion in this section, and are disclosed for the sole purpose of enriching the understanding of the origins and the background of the present invention.

The present invention focuses on harnessing the beneficial biological factors from patients' own blood cells, called platelets. Platelets represent the smallest components of the human blood that assist in blood clotting. Specifically, platelets are fragments of cytoplasm that are derived from the megakaryocytes of the bone marrow. The formation of platelets is governed by the amount of oxygen in the blood and the presence of nucleic acid derivatives from injured tissue. A normal platelet count in a human body ranges from 150,000 to 450,000 platelets per microliter of blood.

The beneficial biological factors secreted by platelets known to be important in healing, regeneration and pain reduction include: 1) platelet-derived growth factors (PDGF), benefiting the collagen production, repair and generation of new blood cells; 2) vascular endothelial growth factor (VEGF), contributing to the growth and generation of new vascular endothelial cells; 3) fibroblast growth factor (FGF), contributing to tissue repair, cell growth and collagen production; 4) epidermal growth factor (EGF), contributing to the growth of the epithelial cells, promotion of new blood cells and wound healing process; 5) transforming growth factor beta 1 (TGF-B), promoting healing of wounds, and contributing to the growth of epithelial and endothelial cells; 6) keratinocyte growth factor (KGF), contributing to the growth and generation of new keratinocytes cells (the predominant cells in the outer layer of skin).

The regenerative properties of platelets have been utilized widely—with varying results—in treatment of various physical conditions, including arthritis, pain management, ligaments, muscle, bone and soft tissue injuries. One of the most popular treatments, currently available on the market, is the platelet rich plasma (PRP) treatment.

The PRP treatment, as the name implies, combines the blood plasma with high levels of platelets, derived from the patient's own blood. The PRP is given to patients through an injection, which could be quite painful. Another drawback of the PRP treatment is its limited shelf life. The limited shelf life of PRP is attributed to the live cells present in the PRP, and also because it clots easily. This drawback requires the patients to undergo the treatment soon after the PRP is prepared; and in circumstances where multiple doses of the PRP are required, forcing the patient to undergo multiple blood draws to complete the PRP treatment.

The present invention addresses the above-defined drawbacks by creating a new treatment supernatant, rich in growth platelet-based factors, but void of any live blood cells—commonly referred to as the enriched platelet factors (EnPLAF). Similarly to the PRP, the EnPLAF supernatant is also created from the patient's own blood. Unlike the PRP, the EnPLAF treatment injections are painless and the EnPLAF supernatant can be easily stored for extended periods of time, even frozen, allowing patients to receive multiple treatments from a single blood draw.

The therapeutic applications of the EnPLAF treatment include: 1) orthopedics and pain management; here, the EnPLAF treatment may accelerate repair and restoration of worn-out joints, soft tissue injuries and reduce pain associated with arthritis, tendinitis, including acute and/or chronic muscle pains; 2) podiatry and wound healing; here, the EnPLAF treatment may alleviate ankle pain, spurs, diabetic ulcers, and accelerate post-surgery recovery times; 3) aesthetic medicine; here, the EnPLAF treatment may contribute to rejuvenation of facial skin, neck, hands, breasts and hair restoration; 4) sexual health; here, the EnPLAF treatment may improve sexual dysfunction as well as increase performance for males when used as an intra-cavernous injection and for females when used as an intra-vaginal injection; 5) dentistry; here, the EnPLAF treatment may accelerate the curative process associated with dental implants, bone grafts, tooth extractions and other periodontal treatments.

BRIEF SUMMARY OF THE INVENTION

The following is intended to be a brief summary of the invention and is not intended to limit the scope of the invention:

The present invention, called the enriched platelet factors (EnPLAF) treatment, is a method of extracting, from the patient's own blood, enriched platelet factors and application thereof in treatment of said patient's various medical conditions; including but not limited to pain management, bone, muscle and soft tissue healing. The foundation of the present invention rests on creation of a new medical supernatant, rich in platelet-based growth factors, but void of any live blood cells. The EnPLAF treatment injections are painless and the EnPLAF can be easily stored for extended periods of time, even frozen, allowing patients to receive multiple treatments from a single blood draw.

DESCRIPTIVE KEY

100—The Enriched Platelet Factors (EnPLAF) Treatment Cycle
  200—Conduct Informational Meeting
    210—Physician's or Aesthetician's Office
    220—Standardized Informational Methods (Verbal & Visual Presentations)
    230—Conducted by the Doctor or Other Authorized Personnel
  300—Evaluate the Patient
    310—Evaluate the Patient's General Physical Condition
    320—Evaluate Production of Platelets; Assess the Patient's Ability to Create Platelet Factors by Looking for the Following Negative Conditions:

321—Pregnancy Causing Thrombocytopenia
322—Lupus Causing Immune Thrombocytopenia
323—Rheumatoid Arthritis Causing Immune Thrombocytopenia
324—Blood Bacteria
325—Thrombotic Thrombocytopenic Purpura
326—Hemolytic Uremic Syndrome
327—Platelets Eliminating Medications (i.e. heparin, quinine, sulfa-containing antibiotics and anticonvulsants)
328—Platelet Count <105/ul
329—Low Hemoglobin Count <105 K/ul
330—Evaluate Relative Treatment Contraindicators; Assess the Patient's Ability to Accept the Platelet Treatment by Looking for the Following Contraindicators:
331—Consistent Use of NSADs 48 Hrs Before the Treatment
332—Injection of Corticosteroid at Treatment Site Within 1 Month Before the Treatment
333—Systematic use of Corticosteroid Within 2 Weeks Before the Treatment
334—Use of Tobacco
335—Recent Fever or Illness
336—Cancer
340—Evaluate Absolute Treatment Contraindicators; Assess the Patient's Ability to Accept the Platelet Treatment by Looking for the Following Contraindicators:
341—Platelet Disfunction Syndrome
342—Critical Thrombocytopenia
343—Hemodynamic Instability
344—Septicemia
345—Infection at the Site of the Procedure
346—Patient's Unwillingness to Accept the Risk of the Procedure
350—Doctor Completes Further Assessment of the Patient's Condition and its Ability to Receive the Platelet Factors Treatment
400—Complete the Venipuncture Procedure
410—Veinpuncture Methods
411—Winged infusion method
412—Syringe needle method
413—Vacuum tube method
420—Veinpuncture Systems
421—Blood Drawing Trays (protective gloves, needles, antiseptics, tourniquets, collection tubes, sharp's containers)
500—Review the Enriched Platelet Factors Extraction Procedure (first step in ensuring availability of the necessary equipment for extraction of the Enriched Platelet Factors)
501—Place the patient's blood into a heparinized vacutainer tube
502—Mix the patient's blood well by inverting the tube 4-5 times
503—Centrifuge the tube at room temperature @ 2000 rpm for 20 minutes
504—Remove the supernatant (plasma) from the tube, leaving only approximately 1 cc plasma in the vacutainer tube
505—Add 100 units of Reagent A (Pharmaceutical grade Thrombin)
506—Mix the blood well
507—Incubate for minimum 1 hour @ 37° C.
508—Add 2 cc Saline or Ringer Lactate
509—Centrifuge the tube at room temperature @ 2000 rpm for 20 minutes
510—Remove the supernatant which is Enriched Platelet Factors (EnPLAF)
600—Review Availability of the Equipment Necessary for Extraction of the Enriched Platelet Factors
601—Sodium Heparin Vacutainer tube 16×100 mm for blood collection
602—Vacutainer Safety-Loc with Luer Adapter & 12 Inch Tubing for blood draw
603—Swing out Bench Top Centrifuge
604—Sterile filter needle to break the vacuum in vacutainer tube
605—Sterile needle 22 gauge 2.75 inch length to withdraw and/or re-introduce plasma/EnPLAF
606—Syringes 5 cc
607—Reagent A (Pharmaceutical grade Thrombin)
608—Incubator which can maintain 37° C.
609—Reagent B (Saline or Ringer Lactate)
610—Cryogenic vials to store EnPLAF
700—APPLY THE ENRICHED PLATELET FACTORS (EnPLAF) EXTRACTION METHOD
701—Draw the patient's blood and place in the vacutainer tube
702—Mix the patient's blood in the centrifuge
703—Put sterile filter needle in the vacutainer tube
704—Put sterile 22 g 2.75 inch needle in vacutainer tube
705—Withdraw all plasma, then re-introduce 1 cc plasma
706—Add 100 units Reagent A
707—Remove the 22 g 2.75 inch needle
708—Mix well and place it in Incubator for 1 hr @ 37° C.
709—Re-introduce 22 g 2.75 inch needle
710—Add 2 cc Reagent B
711—Remove the 22 g 2.75 inch needle
712—Mix well and centrifuge
713—Introduce new 22 g needle
714—Remove supernatant using 22 g needle
715—Place Enriched Platelet Factors in a vial for storage or immediate application
800—Methods of Administrating the Platelet Factors to the Patient
801—Administer as an injection of autologous growth factors, directly into the patient's affected area (may be utilized for treatment of: sexual dysfunctions, podiatric issues, healing associated with dental treatments, pain management, general wound healing, orthopedic problems, aesthetic issues, including breasts rejuvenation and hair restoration);
802—Administer by mixing with a cream base to be used as an at-home, non-injection alternative (may be utilized for treatment of: aesthetic-related conditions and general wound healing);
803—Administer in the form of a wound healing patch, designed to deliver autologous growth factors directly to the problem area (may be utilized for treatment of: aesthetic-related conditions and general wound healing);
804—Administer in a form of a topical medication with local therapeutics (may be utilized for treatment of: aesthetic-related conditions, pain reduction, healing of minor burns and scars);
805—Administer, utilizing any of the above-listed methods, to deliver autologous growth factors directly to the problem area during the preoperative and postoperative phases of surgery (e.g. may be utilized for treatment of aesthetic-related conditions, pain and for acceleration of healing process).

BRIEF DESCRIPTION OF THE DRAWINGS

The components shown in the drawings are not to scale. In the interest of clarity, some of the components might be shown in a generalized form and could be identified utilizing commercial designations. All components, including its essential features, have been assigned reference numbers that are utilized consistently throughout the descriptive process outlined herein.

DETAILED DESCRIPTION AND BEST MODE OF IMPLEMENTATION

The following description references to the above-defined drawings and represents only an exemplary embodiment of the invention. It is foreseeable, and recognizable by those skilled in the art, that various modifications and/or substitutions to the invention could be implemented without departing from the scope and the character of the invention:

The present invention, outlined in FIGS. 1-7, discloses a method of extracting, from the patient's own blood, enriched platelet factors ("EnPLAF") 700 and application thereof in treatment 100 of said patient's medical conditions, including but not limited to pain management, bone, muscle and soft tissue healing.

Figure 1:
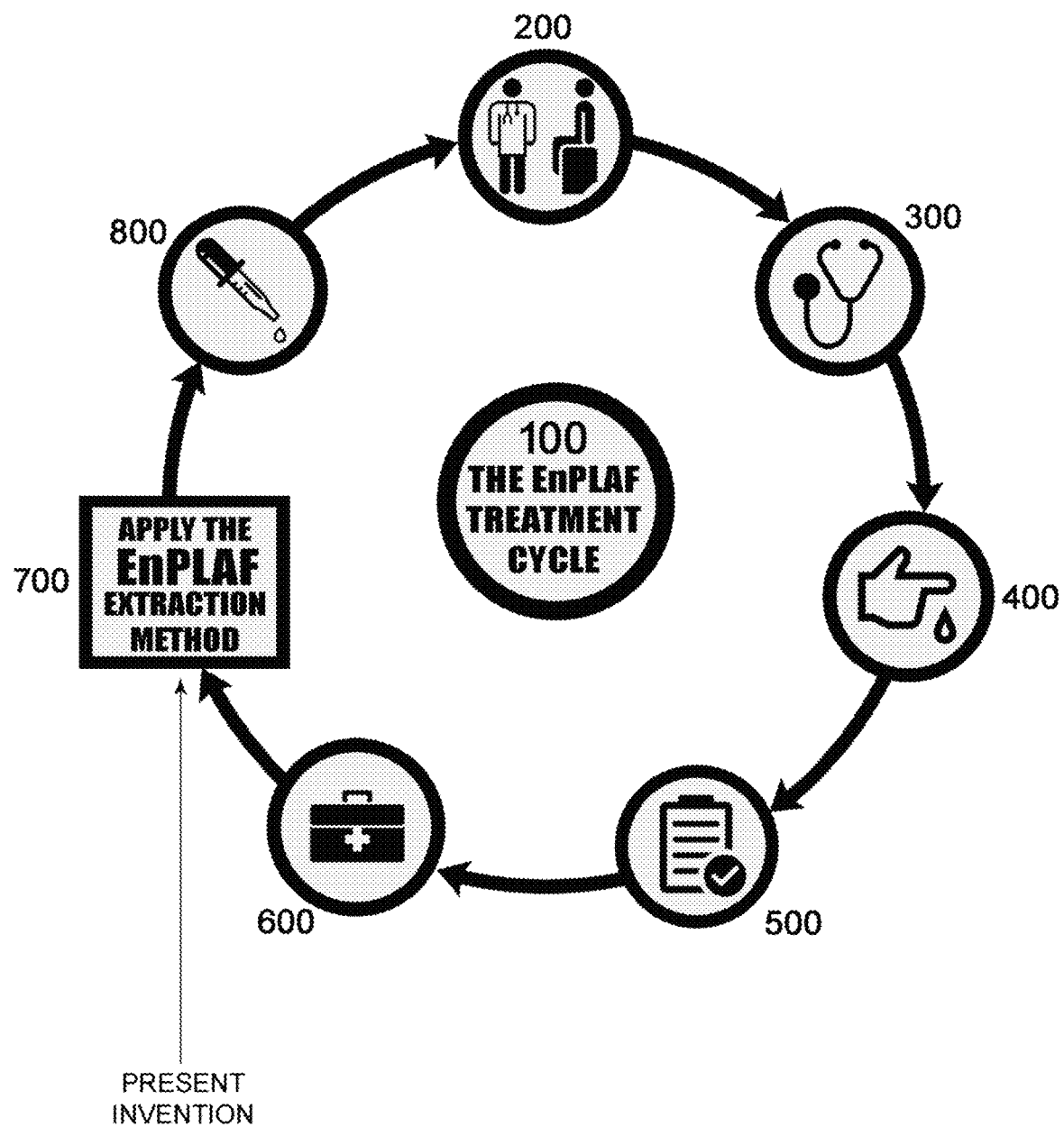
FIG. 1 is an illustrative diagram showing the enriched platelet factors treatment cycle, focusing on extraction and application of the of the enriched platelet factors to a patient, in accordance with an exemplary embodiment of the present invention.
Figure 2:
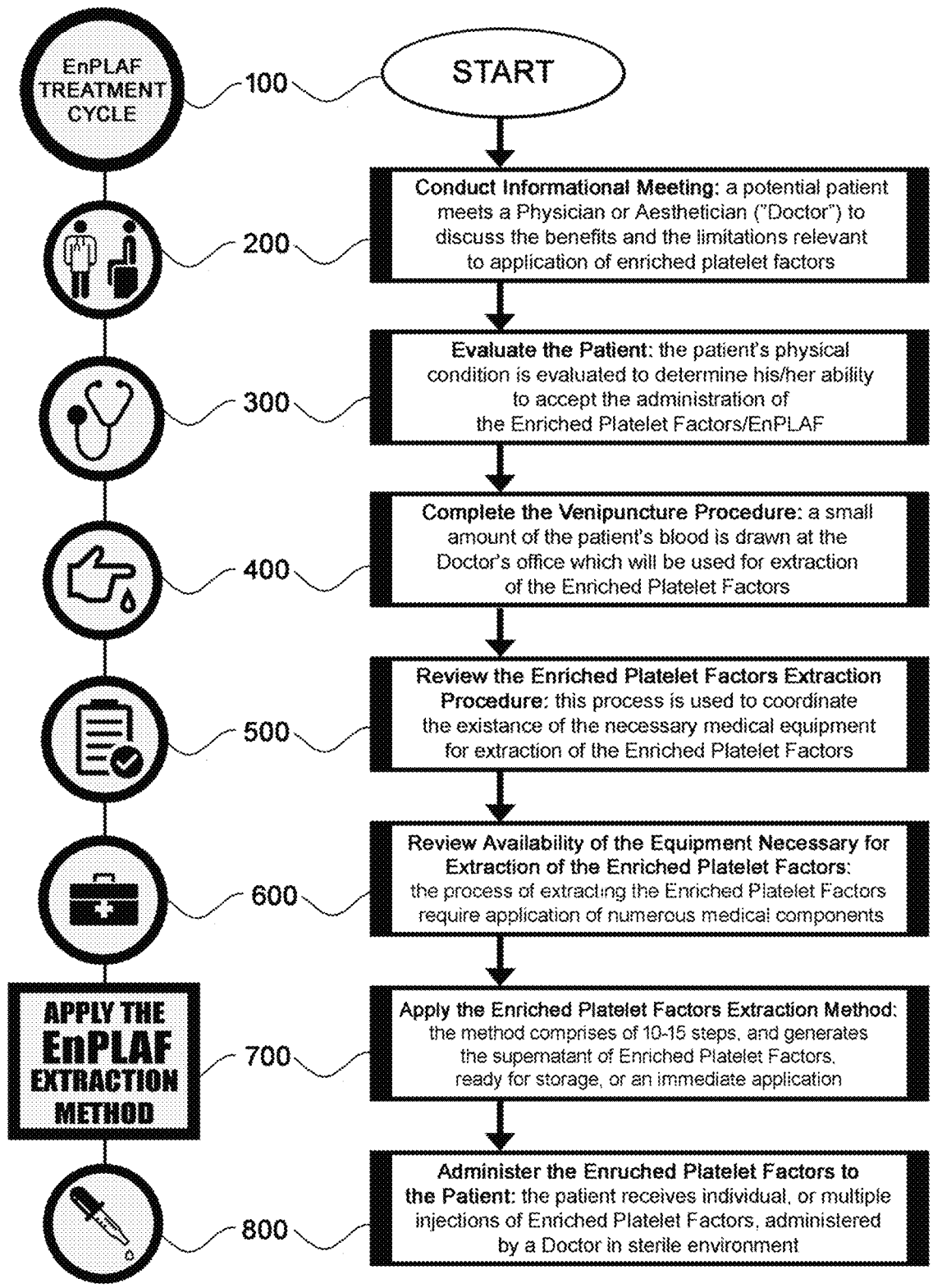
FIG. 2 is a flowchart diagram illustrating the general step undertaken during the application of the enriched platelet factors treatment cycle, in accordance with an exemplary embodiment of the present invention.

As shown in FIG. 1 shows the EnPLAF treatment cycle, and FIG. 2, shows the process of implementing the EnPLAF treatment 100. The treatment starts with an informational meeting 200, conducted in a controlled environment of a medical office 210, by a physician, aesthetician 230 and/or other authorized individual. The information provided during the meeting 200 may be communicated utilizing standardized information methods 220, including but not limited to verbal and visual presentations. The purpose of the meeting is to inform the potential patient about the benefits and the drawbacks of the EnPLAF treatment 100.

Figure 3:
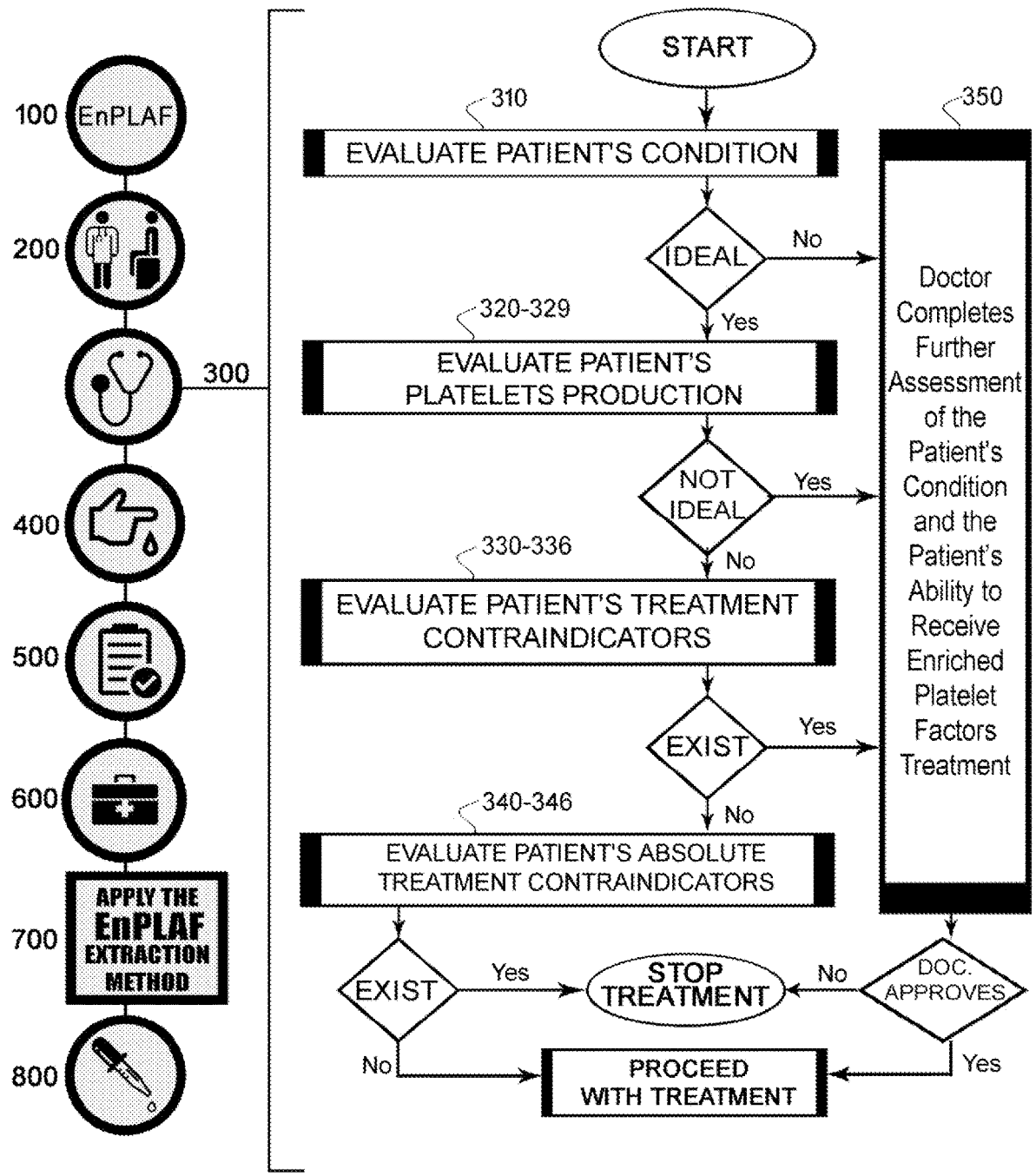
FIG. 3 is a flowchart diagram illustrating the logical process undertaken during the doctor's evaluation of the patient, intended to determine said patient's ability to accept the platelet factors treatment, in accordance with an exemplary embodiment of the present invention.

Once the informational session 200 has been completed, the physician 230, or other authorized individual, evaluates the patient's physical condition 300 to determine his/her ability to accept the EnPLAF treatment 100 (Ref. FIGS. 1, 2 and 3). Here, the patent's general physical condition is assessed 310, followed by evaluation of the patient's ability to produce platelets 320-329. The evaluation 300 focuses directly on both the patient's relative 330 and absolute 340 treatment contraindicators.

The relative 330 treatment contraindicators, assess the potential patient's ability to accept the EnPLAF treatment 100 by looking for the following conditions: 1) consistent use of NSAIDs 331 48 hours before the treatment 100; 2) injection of corticosteroid 332 at treatment site within 1 month before the treatment 100; 3) systematic use of corticosteroid 333 within 2 weeks before the treatment 100; 4) use of tobacco 334; 5) recent fever or illness 335; 6) cancer 336. The uncovered, relative 330 treatment contraindicators are meticulously analyzed by the physician 230, who will ultimately makes the final determination 350, specifying whether the patient may, or may not, receive the EnPLAF treatment 100 (Ref. FIG. 3).

The absolute 340 treatment contraindicators, assess the potential patient's ability to accept the EnPLAF treatment 100 by looking for the following conditions: 1) Platelet Disfunction Syndrome 341; 2) Critical Thrombocytopenia 342; 3) Hemodynamic Instability 343; 4) Septicemia 344; 5) Infection at the Site of the Procedure 345; 6) Patient's Unwillingness to Accept the Risk of the Procedure 346. The revealed relative 330 treatment contraindicators will prevent the patient from participating in the EnPLAF treatment 100 (Ref. FIG. 3).

Once the patient's ability to participate in the EnPLAF treatment 100 is confirmed, the physician (or other authorized individual) collects the patient's blood, which will be utilized to extract the enriched platelet factors (Ref. FIGS. 1 and 2). The blood may be collected from the patient by utilizing various techniques, including but not limited to available veinpunctre methods 410 (i.e. winged infusion 411, needle/syringe 412 and vacuum tube 413 methods).

Figure 4:
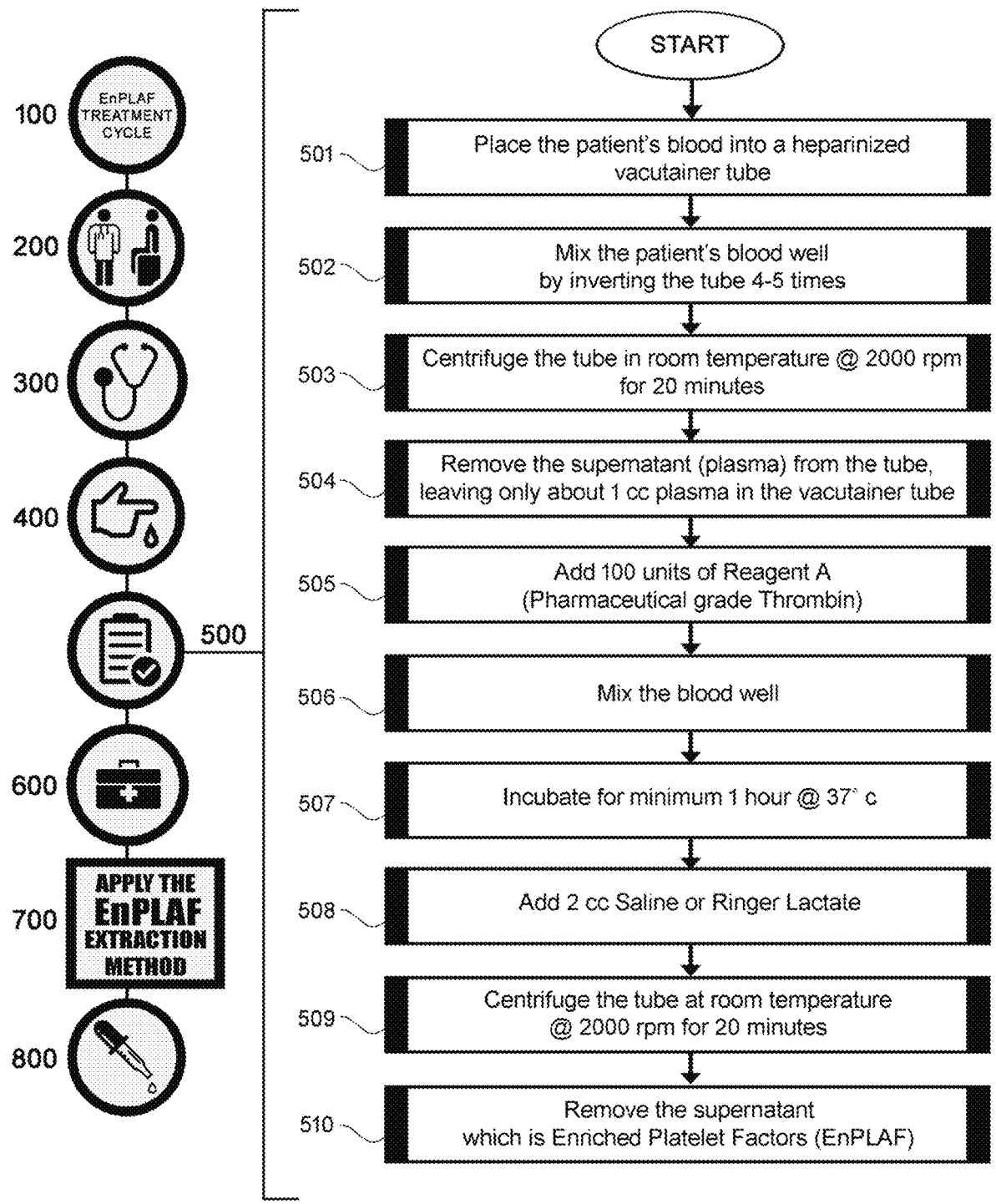
FIG. 4 is a flowchart diagram illustrating the review of the enriched platelet factors extraction procedure, focusing on determining the existence of the necessary medical equipment for extraction of the enriched platelet factors, in accordance with an exemplary embodiment of the present invention.
Figure 5:
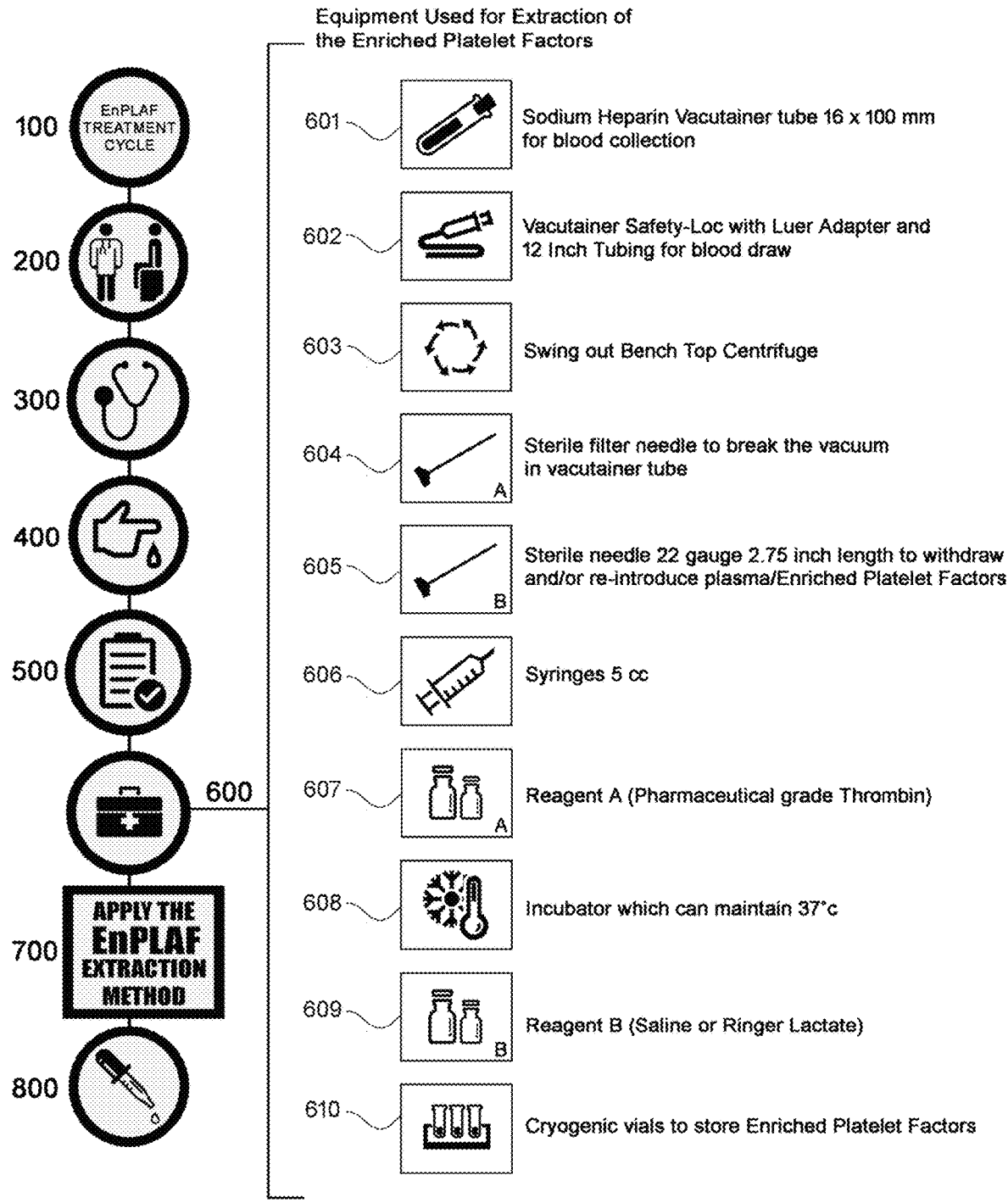
FIG. 5 is an illustrative diagram, listing the equipment used for extraction of the enriched platelet factors, in accordance with an exemplary embodiment of the present invention.
Figure 6:
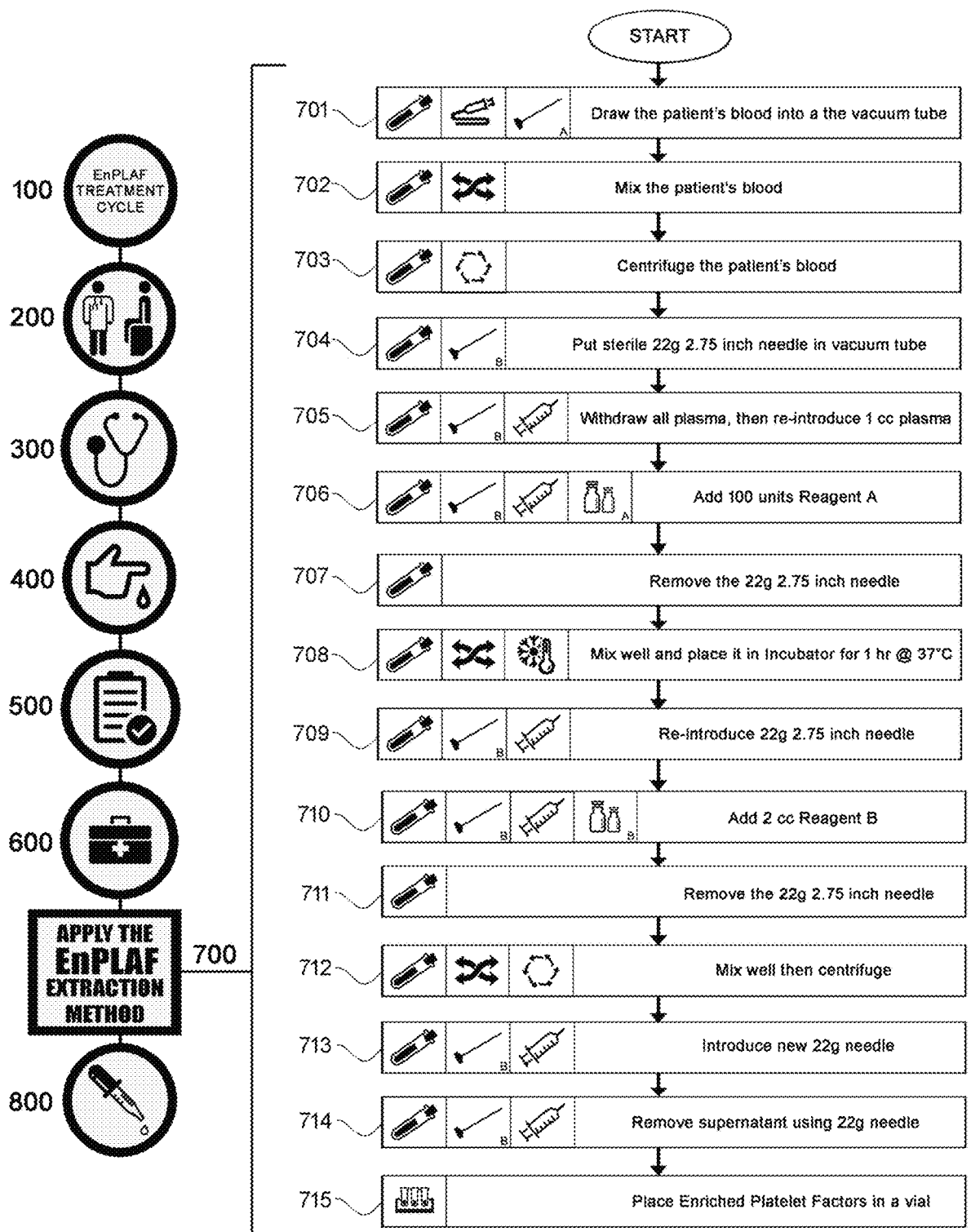
FIG. 6 is an illustrative diagram showing the method used for extraction of the enriched platelet factors, in accordance with an exemplary embodiment of the present invention.

Next, in accordance with the method for extracting the enriched platelet factors 500 and 700, the patient's blood is placed into a heparinized vacutainer tube 501/701 (Ref. FIGS. 4, 5 and 6). Once in the tube 501/701, the blood should be well mixed by inverting the tube 4-5 times 502/702. The blood is then centrifuged in room temperature at 2000 RPM for 20 minutes 503/703. Most of the supernatant (plasma) is then taken out of the vacutainer tube, using a needle 704, and thrown out, leaving approximately 1 cc of plasma 504/705. Next, the vacutainer tube is infused with 100 units of Reagent A (pharmaceutical grade Thrombin) 505/706. Upon completion of this procedure, the blood is once again mixed manually 506/708, and is thereafter placed in an incubator, capable of maintaining the temperature of 37° C. for a period of one hour 507/708. Upon removal from the incubator, using a needle 709, the blood is infused with Reagent B, or 2 cc of saline or ringer lactate 508/710, and once again the blood is placed inside of the centrifuge that is operated in room temperature at 2000 RPM for 20 minutes 509/712. Once the centrifuge operation is completed, the process of extracting the enriched platelet factors 700 is finalized, and ready for the administrative procedures 800.

Figure 7:
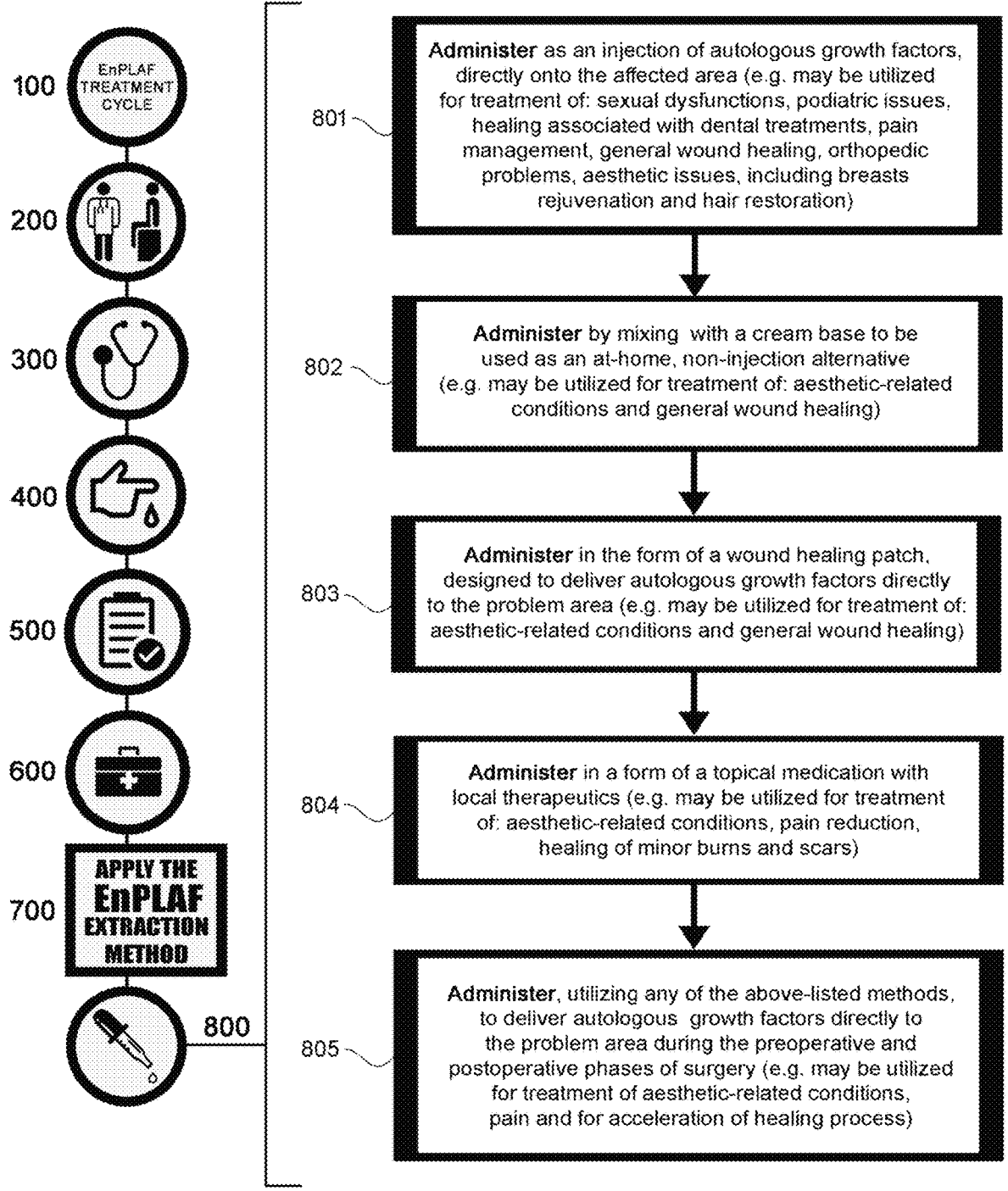
FIG. 7 is a flowchart diagram illustrating various methods of administering to the patient, the enriched platelet factors and their applicable treatments, in accordance with an exemplary embodiment of the present invention.

As shown in FIG. 7, the formulated supernatant containing the EnPLAF 700, may be administered to a patient to treat numerous medical conditions. The methods 800 of administering the EnPLAF treatment 100, including but not limited to:

1) injection of autologous growth factors, directly into the patient's affected area (e.g. this application may be utilized for treatment of sexual dysfunctions, podiatric issues, healing associated with dental treatments, pain management, general wound healing, orthopedic problems, aesthetic issues, including breasts rejuvenation and hair restoration) 801;

2) mixing the EnPLAF 700 with a cream base, which may be utilized at-home as a non-injection alternative (e.g. this application may be utilized for treatment of aesthetic-related conditions and general wound healing) 802;

3) applying the EnPLAF 700 in the form of a wound healing patch, designed to deliver autologous growth factors directly to the problem area (e.g. this application may be utilized for treatment of aesthetic-related conditions and general wound healing) 803;

4) applying the EnPLAF 700 in the form of a topical medication with local therapeutics (e.g. this application may be utilized for treatment of aesthetic-related conditions, pain reduction, healing of minor burns and scars) 804;

5) utilizing any of the above-listed methods, to deliver autologous growth factors directly to the problem area during the preoperative and postoperative phases of surgery (e.g. this application may be utilized for treatment of aesthetic-related conditions, pain and to accelerated the healing process) 805.

What is claimed is:

1. A method of extracting enriched platelet factors from human blood, comprising:
   a. providing means of extracting 10 cc of human blood from a patient,
   b. providing a vacutainer tube for collection of said human blood which is able to retain said blood when mixed by manually inverting the vacutainer tube or by using a mechanical centrifuge,
   c. mixing the human blood in said vacutainer tube by manually inverting the vacutainer tube four or five times,
   d. providing a mechanical centrifuge, situated in room temperature, which can rotate the vacutainer tube, containing the human blood, continuously for 20 minutes at 2000 rpm causing buildup of plasma,
   e. providing means of removing the plasma from the vacutainer tube, which will allow to leave in said vacutainer tube 1 cc of the created plasma
   f. providing means of inserting into the vacutainer tube reagent A, which will allow for insertion into the vacutainer tube 100 units of pharmaceutical-grade Thrombin, Page 15 of 18
   g. mixing blood cells, platelets, plasma and the pharmaceutical-grade Thrombin in said vacutainer tube by manually inverting the tube four or five times,
   h. providing an incubator which can store the vacutainer tube, containing the plasma mixed with the blood cells, platelets, and pharmaceutical-grade Thrombin, for 1 hour at a temperature equivalent to 37° C.,
   i. providing means of inserting into the vacutainer tube reagent B, which will allow for insertion into the vacutainer tube, containing the plasma mixed with the blood cells, platelets, and pharmaceutical-grade Thrombin, 2 cc of saline or ringer lactate,
   j. rotating the vacutainer tube, containing the plasma mixed with the blood cells, platelets, pharmaceutical-grade Thrombin and saline, in said centrifuge at room temperature continuously for 20 minutes at 2000 rpm, creating a separation of supernatant,
   k. extracting the supernatant from said vacutainer tube, which is enriched platelet factors,
   l. using said enriched platelet factors for bone healing,
   m. using said enriched platelet factors for muscle healing,
   n. using said enriched platelet factors for tissue healing,
   o. administering enriched platelet factors to the patient as an injection,
   p. administering enriched platelet factors to the patient topically as a cream base,
   q. administering enriched platelet factors to the patient topically as a healing patch.

* * * * *